United States Patent [19]
Cavazza

[11] Patent Number: 5,683,712
[45] Date of Patent: Nov. 4, 1997

[54] TRANSDERMAL PATCH FOR THE ADMINISTRATION OF HOMEOPATHIC DRUGS

[75] Inventor: Paolo Cavazza, Rome, Italy

[73] Assignee: Avantgarde S.p.A., Rome, Italy

[21] Appl. No.: 528,162

[22] Filed: Sep. 14, 1995

Related U.S. Application Data

[63] Continuation of Ser. No. 291,030, Aug. 16, 1994, abandoned.

[30] Foreign Application Priority Data

Sep. 2, 1993 [IT] Italy .................................. RM93A0591

[51] Int. Cl.⁶ .................................................. A61F 13/02
[52] U.S. Cl. ............................................. 424/449; 424/448

[58] Field of Search ........................................ 424/448, 449

[56] References Cited

U.S. PATENT DOCUMENTS 5,330,756   7/1994   Steuart et al. ........................ 424/405

Primary Examiner—Jyothsna Venkat
Attorney, Agent, or Firm—Oblon, Spivak, McClelland, Maier & Neustadt, P.C.

[57] ABSTRACT

Medical device for the administration of active ingredients or drugs at very low doses, and particularly of homeopathic drugs, comprising a transdermal patch with a support membrane, a layer of porous adhesive, a microporous membrane and a gel containing the homeopathic drug to be administered.

4 Claims, 1 Drawing Sheet

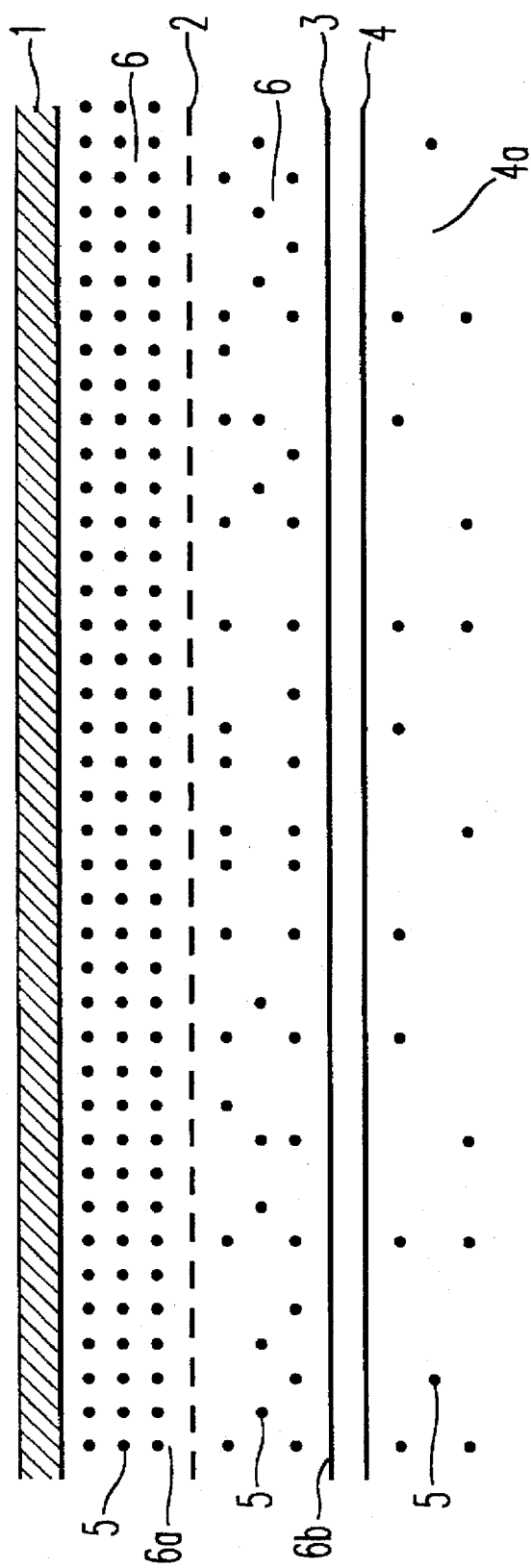

TRANSDERMAL PATCH FOR THE ADMINISTRATION OF HOMEOPATHIC DRUGS

This application is a Continuation of application Ser. No. 08/291,030, filed on Aug. 16, 1994, now abandoned.

The present invention relates to a medical device for the administration of drugs or active ingredients at low concentrations, and particularly for the administration of homeopathic drugs.

As is well known, homeopathy is a therapeutic approach based on the concept that disease conditions should be cured by administering drugs which, in healthy people, induce a symptom picture similar to that manifested by the disease one intends to treat. Also typical of homeopathic treatment is that extremely low, and sometimes infinitesimal doses of the homeopathic remedy must be given in order to induce the desired therapeutic effect, whereas high doses of the same drug would actually cause the symptom picture of the disease one is seeking to cure.

Homeopathic preparations are traditionally prepared by means of a method (called "potentization") consisting in a succession of dilutions and succussions of the drug solution; part of the drug (of a vegetable, animal, mineral or synthetic nature) is dissolved (or ground according to the substance) in nine parts of distilled water or alcohol and the resulting mixture is shaken vigorously. Nine parts of this initial solution are taken and diluted with nine parts of water or alcohol and the resulting second diluted solution is again subjected to vigorous succussion. This stage of dilution and succussion can subsequently be repeated several times. Standard potentization levels include the 3× (three times), 6×, 200×, 1000× dilutions, etc. A homeopathic preparation therefore presents itself generally in the form of an extremely dilute solution (aqueous, alcoholic or hydro-alcoholic) of active ingredient.

This type of pharmaceutical formulation severely conditions the mode of administration of homeopathic preparations, limiting it to the oral administration of a number of drops of solution, repeated at one-hourly intervals or, at least, several times a day. Furthermore, to achieve maximum efficacy, the drops of solution must be placed under the tongue and held there for a certain amount of time before being swallowed. For example (see "Applied Homeopathy" by R. Jacobs and M. E. Pinkerson. Homeopathy Press, Santa Monica, Calif., 1983), 10–15 drops of a homeopathic drug for the treatment of neuralgia and sciatica (consisting of Belladonna 6×, Spigelia 6×, Mag.phos. 6×, and Cimifuga 6×) are administered until symptoms are reduced and thereafter the same dose is given 4 times daily until symptoms disappear, holding the solution each time under the tongue for 30 seconds before swallowing it. It will be noted that, though it is advisable to spread the drops of the homeopathic preparation under the patient's tongue, this is still a form of oral and not a form of percutaneous administration, as occurs with sublingual tablets, inasmuch as the solution is actually swallowed after a short space of time.

Sublingual tablets are also used for the administration of homeopathic drugs and present the same drawbacks as already described for solutions.

It is clear that these administration methods, and in particular the need for frequent administrations and for holding the drops of the preparation or the sublingual tablets under the tongue make compliance difficult for any type of patient and particularly difficult for disabled persons, elderly patients and children.

The aim of the invention described herein is to provide a means or, to be more precise, a medical device for the administration of active ingredients or drugs at very low doses, particularly homeopathic drugs, which overcomes the drawbacks mentioned above. According to the invention, the homeopathic drug is administered via the trandsdermal route by means of a patch which is applied to the skin in a preselected area of the body. The structure of an example of a trandsdermal patch which can be used to achieve the aims of the present invention is illustrated in the figure attached hereto. With reference to the figure, which represents the patch in the position of use, i.e. as applied to the patient's skin, the transdermal patch presents a sandwich-type structure with support membrane 1 on the outer surface of the patch distal to the patient's skin and a layer of porous adhesive (e.g. silicone) 3 on the opposite side which defines the contact surface of the patch with the epidermis 4 of the area of the body chosen for the application.

Between support membrane 1 and porous adhesive layer 3 there is a microporous membrane 2 which controls the release of drug 5. Drug 5 is scattered in a gel consisting of glycerine, distilled water, lactose, poly(vinyl alcohol), poly(vinyl-2-pyrrolidone) and sodium citrate. To be more precise, the gel zone 6a situated between support membrane 1 and microporous membrane 2 acts as a drug reservoir so that the concentration of drug in this zone is maximal, whereas, as a result of the effect of membrane 2, the drug concentration in gel zone 6b below the membrane is lower, while the drug concentration in the subcutaneous zone 4a is even lower owing to the regulatory effect which the skin itself exerts on the spread of the drug. (In the figure, the progressively decreasing concentration of the drug in zones 6a, 6b and 4a, respectively, is represented schematically by a correspondingly decreasing density of dots denoting molecules of drug).

To sum up, then, the medical device for the administration of active ingredients or drugs at very low doses, and particularly of homeopathic drugs, according to the invention consists in a transdermal patch characterized by the following components:

a) a support membrane 1 defining the outer surface of the patch distal to the skin area chosen for the application;

b) a layer of porous adhesive 3 on the opposite side of the patch defining the contact surface between the patch and the skin 4;

c) a microporous membrane 2 for controlling the release of the drug, placed between support membrane 1 and porous adhesive layer 3; and d) a gel 6 containing, scattered within it, the homeopathic drug 5 to be administered.

The microporous membrane 2 defining, above it, a gel zone 6a acting as a reservoir for the drug, and, below it, a gel zone 6b in which the drug concentration is lower than that in zone 6a.

The patch can be applied on any suitable skin area, chosen, among other things, in relation to the symptom picture to be resolved, if possible hairless, avoiding skin folds and areas of scarred, burnt or irritated skin.

There can be no mistaking the substantial advantages to be gained with this administration device compared to the traditional mode of administration of homeopathic drugs:

(1) it avoids the need for multiple, repeat administrations in the course of the day at short intervals one from another;

(2) mono-administration and, above all, not having to hold the preparation (whether in solution or sublingual tablet form) under the tongue enormously facilitates patient compliance, particularly in the case of disabled persons, elderly patients and children;

(3) compliance is also facilitated by the fact that the patient does not have to make any kind of effort of will or take part actively, since, particularly in the case of disabled persons and children, the application of the patch on the patient's skin can be done by some other person;

(4) administration of the drug can be interrupted at any time it may be so desired;

(5) the administration is more effective owing to the slow release of the drug.

I claim:

1. A transdermal patch, comprising:

a) a porous adhesive layer for contacting skin epidermis;

b) a first gel layer containing a homeopathic drug on said porous adhesive layer;

c) a second gel layer containing said homeopathic drug on said first gel layer;

d) a microporous membrane between said first and second gel layers for controlling release of said homeopathic drug from said second gel layer into said first gel layer such that the concentration of said homeopathic drug in said first gel layer is lower than the concentration of said homeopathic drug in said second gel layer; and e) a support membrane on said second gel layer.

2. The patch of claim 1, wherein said first and second gel layers contain glycerin, water, lactose, poly(vinyl)alcohol, poly(vinyl-2-pyrrolidone) and sodium citrate.

3. The patch of claim 1, wherein said porous adhesive layer is a silicone adhesive.

4. The patch of claim 1, wherein said support membrane defines the outer surface of said transdermal patch.

* * * * *